US010576060B2

(12) United States Patent
Yoon et al.

(10) Patent No.: US 10,576,060 B2
(45) Date of Patent: Mar. 3, 2020

(54) FK506 DERIVATIVE MAINTAINING NERVE REGENERATION ACTIVITY WITHOUT IMMUNOSUPPRESSIVE ACTIVITY, AND USE THEREOF

(71) Applicant: INTRON BIOTECHNOLOGY CO., LTD, Seongnam-si (KR)

(72) Inventors: Yeo Joon Yoon, Seoul (KR); Ho Jeong Kwon, Seoul (KR); Yeon Hee Ban, Seoul (KR); Shinde Pramodb, Seoul (KR)

(73) Assignee: INTRON BIOTECHNOLOGY CO., LTD, Seongnam-si (KR)

(*) Notice: Subject to any disclaimer, the term of this patent is extended or adjusted under 35 U.S.C. 154(b) by 0 days.

(21) Appl. No.: 16/242,386

(22) Filed: Jan. 8, 2019

(65) Prior Publication Data
US 2019/0134001 A1    May 9, 2019

Related U.S. Application Data

(63) Continuation of application No. 15/500,353, filed as application No. PCT/KR2015/008031 on Jul. 31, 2015, now Pat. No. 10,226,446.

(30) Foreign Application Priority Data

Aug. 1, 2014    (KR) .................. 10-2014-0099210

(51) Int. Cl.
  *A61K 31/4025*    (2006.01)
  *A61K 31/436*    (2006.01)
  *C12P 17/16*    (2006.01)

(52) U.S. Cl.
  CPC ........ *A61K 31/4025* (2013.01); *A61K 31/436* (2013.01); *C12P 17/16* (2013.01)

(58) Field of Classification Search
  CPC .... A61K 31/401; A61K 31/4025; C12P 17/16
  See application file for complete search history.

(56) References Cited

U.S. PATENT DOCUMENTS

| 4,894,366 A | 1/1990 | Okuhara et al. |
| 9,855,253 B2 | 1/2018 | Bahn |
| 10,226,446 B2 * | 3/2019 | Yoon .................. A61K 31/4025 |
| 2008/0161248 A1 | 7/2008 | Robbins |
| 2013/0230559 A1 | 9/2013 | Yoon et al. |

FOREIGN PATENT DOCUMENTS

| CN | 101573109 A | 11/2009 |
| KR | 10-1261131 B1 | 5/2013 |

OTHER PUBLICATIONS

Andexer et al., "Biosynthesis of the immunosuppressants FK506, FK520, and rapamycin involves a previously undescribed family of enzymes acting on chorismate,"*PNAS* 108(12):4776-4781 (Mar. 22, 2011).
Ban et al., "Characterization of FK506 Biosynthetic Intermediates Involved in Post-PKS Elaboration," *Journal of Natural Products* 76:1091-1098 (2013).
Chen et al., "FK506 Maturation Involves a Cytochrome P450 Protein-Catalyzed Four-Electron C-9 Oxidation in Parallel with a C-31 O-Methylation," *Journal of Bacteriology* 195(9):1931-1939 (May 2013).
Damasio, "Alzheimer's Disease and related dementias," *Cecil Textbook of Medicine, 20th Edition*, vol. 2, pp. 1992-1996 (1996).
Glaus et ai., "Clinical Strategies to Enhance Nerve Regeneration in Composite Tissue Allotransplantation," *Hand Clin.* 27(4):495-509, pp. 1-21 (21 pages) (2012).
Gold et al., "Immunophilin FK506-Binding Protein 52 (Not FK506-Binding Protein 12) Mediates the Neurotrophic Action of FK506," *The Journal of Pharmacology and Experimental Therapeutics* 289:1202-1210 (1999).
Gold, "Neuroimmunophilin ligands: evaluation of their therapeutic potential for the treatment of neurological disorders," *Exp. Opin. Invest. Drugs* 9(10):2331-2342 (2000).
Goulet et al., "The medicinal chemistry of FK-506," *Perspectives in Drug Discovery and Design* 2:145-162 (1994).
Griffith et al., "X-Ray Structure of Calcineurin Inhibited by the Immunophilin-Immunosuppressant FKBP12-FK506 Complex," *Cell* 82:507-522 (Aug. 11, 1995).
Kang et al., "FKBP Family Proteins: Immunophilins with Versatile Biological Functions," *Neurosignals* 16:318-325 (2008).
Kino et al., "FK-506, A Novel Immunosuppressant Isolated from a Streptomyces," *The Journal of Antibiotics* XL(9):1249-1255 (Sep. 1987).
Layzer, "Degenerative Diseases of the Nervous System," *Cecil Textbook of Medicine, 20th Edition*, vol. 2, pp. 2050-2057 (1996).
Marcos et al., "Use of Alemtuzumab and Tacrolimus Monotherapy for Cadaveric Liver Transplantation: With Particular Reference to Hepatitis C Virus," *Transplantation* 78(7):966-971 (Oct. 15, 2004).
Migata et al., "FK506: Anti-Inflammatory Properties," *Current Medicinal Chemistry Anti-Inflammatory & Anti Allergy Agents* 2(3) (1 page) (Abstract) (2003).
Mo et al., "Biosynthesis of the Allymalonyl-CoA Extender Unit for the FK506 Polyketide Synthase Proceeds through a Dedicated Polyketide Synthase and Facilitates the Mutasynthesis of Analogues," *Journal of the American Chemical Society* 133:976-985 (2011).
Motamedi et al., "Characterization of Methyltransferase and Hydroxylase Genes Involved in the Biosynthesis of the Immunosuppressants FK5606 and FK520," *Journal of Bacteriology* 178(17):5243-5248 (Sep. 1996).
Motamedi et al., "Structural organization of a multifunctional polyketide synthase involved in the biosynthesis of the macrolide immunosuppressant FK506," *Eur. J. Biochem.* 244:74-80 (1997).

(Continued)

*Primary Examiner* — Deepak R Rao
(74) *Attorney, Agent, or Firm* — Seed IP Law Group

(57) ABSTRACT

The present invention relates to an FK506 derivative which has reduced immunosuppressive activity but maintains nerve regeneration activity, a preparing method thereof, and a pharmaceutical composition comprising the same for preventing or treating nervous system diseases. A composition comprising 9-deoxo-prolyl-FK506, 31-O-demethyl-FK506, or 9-deoxo-31-O-demethyl-FK506 can promote nerve regeneration and has reduced immunosuppressive activity, thereby reducing side effects in the treatment of nervous system diseases.

5 Claims, 13 Drawing Sheets

(56) References Cited

OTHER PUBLICATIONS

Motamedi et al., "The biosynthetic gene cluster for the macrolactone ring of the immunosuppressant FK506," *Eur. J. Biochem.* 256:528-534 (1998).

Nakagawa et al., "Tacrolimus Has Antifungal Activities against *Malassezia furfur* Isolated from Healthy Adults and Patients with Atopic Dermatitis," *Clin. Drug Invest.* 12(5):244-250 (Nov. 1996).

Park et al., "Liquid chromatography-mass spectrometry characterization of FK506 biosynthetic intermediates in *Streptomyces clavuligerus* KCTC 10561BP," *Analytical Biochemistry* 393:1-7 (2009).

Parsons et al., "FK-506—A Novel Immunosuppressant," *Annals New York Academy of Sciences* (15 pages) (1993).

Revill et al., "Genetically Engineered Analogs of Ascomycin for Nerve Regeneration," *The Journal of Pharmacology and Experimental Therapeutics* 302(3):1278-1285 (2002).

Shafiee et al., "Chemical and Biological Characterization of Two FK506 Analogs Produced by Targeted Gene Disruption in *Streptomyces* sp. MA6548," *The Journal of Antibiotics* 50(5):418-423 (7 pages) (May 1997).

Shinde et ai., "A non-immunosuppressive FK506 analogue with neuroregenerative activity produced from a genetically engineered Streptomyces Strain," *RSC Advances,* 5:6823-6828 (2015).

\* cited by examiner

US 10,576,060 B2

FK506 DERIVATIVE MAINTAINING NERVE REGENERATION ACTIVITY WITHOUT IMMUNOSUPPRESSIVE ACTIVITY, AND USE THEREOF

CLAIM OF PRIORITY

This application is a continuation of U.S. application Ser. No. 15/500,353, filed on Jan. 30, 2017, which is a U.S. national phase application of PCT/KR2015/008031, filed Jul. 31, 2015, which claims priority to Korean Application No. 10-2014-0099210, filed Aug. 1, 2014. U.S. application Ser. No. 15/500,353 is herein incorporated by reference in its entity.

TECHNICAL FIELD

The present invention relates to an FK506 derivative which has reduced immunosuppressive activity but maintains neuroregenerative activity, a preparing method thereof, and a pharmaceutical composition comprising the same for preventing or treating nervous system diseases.

BACKGROUND ART

FK506, also known as tacrolimus or fujimycin, is a 23-member macrocyclic lactam and can be isolated from *Streptomyces tsukubaensis*. FK506 and drugs similar thereto are known to interact with cytoplasmic immunophilin proteins, commonly referred to as FK506-binding proteins (FKBPs), to modify several biochemical reactions (Kang, C. B. et al., Neurosignals 2008).

In particular, FK506 clinically prevents allograft rejection (Kino, H. et al., J. Antibiot. 1987; Kino, H. et al., J. Antibiot. 1987; Fung, J. J. et al., Transplantation 2004) and is used as an immunosuppressant for treating autoimmune diseases such as atopy (Parsons, W. H. et al., Ann. N. Y. Acad. Sci. 1993). FK506 is an important element in signaling of T-cell receptor and suppresses the activity of calcineurin, which suppresses T lymphocyte activity.

In a specific study of the mechanism of immunosuppressive activity of FK506, the chemical structure of FK506 can be divided into two regions: an effector region which binds to calcineurin (Goulet, M. T. et al., Perspect. Drug Discov. 1994; Parsons, W. H. et al., Ann. N. Y. Acad. Sci. 1993; Griffith, J. P. et al., Cell 1995) and a binding site which forms a complex with FKBPs. The FKBP binding site comprises a pipecolate moiety, a tricarbonyl group, and a cyclohexane ring, and plays an important role in complex formation with the FKBP12 protein. This allows the remaining effector region to freely bind to calcineurin so as to form a tripartite complex.

In order to exert the immunosuppressive effect above, it is important that FK506 first binds to the FKBP12 protein. Once the two-part complex is formed, the complex can interact with calcineurin (Goulet, M. T. et al., Perspect. Drug Discov. 1994; Parsons, W. H. et al., Ann. N. Y. Acad. Sci. 1993). The interaction of FK506-FKBPs complex with calcineurin inhibits interleukin-2 mediated by T-cell proliferation, resulting in immunosuppressive action.

FK506 is synthesized by a hybrid PKS/NRPS (polyketide synthase/nonribosomal peptide synthetase) system. The biosynthesis process is carried out using DHCHC (4,5-dihydroxycyclohex-1-ene carboxylic acid), which is derived from chorismate, as a starting material, where DHCHC is extended by 10-step condensation using two molecules of malonyl-CoA, two molecules of methoxymalonyl-acyl carrier proteins (ACP), five molecules of methylmalonyl-CoA, and one molecule of allylmalonyl-CoA (Andexer, J. N. et al., Proc. Natl. Acad. Sci. U.S.A 2011; Mo, S. J. et al., J. Am. Chem. Soc. 2011). Pipecolate derived from lysine by FkbL action is condensed with a linear polyketide chain by NRPS KfbL and is cyclized to produce a macrolide ring. The ring is further modified by a post-PKS modification process such as O-methylation at C-31 caused by FkbM (S-adenosylmethionine (SAM)-dependent methyltransferase) or an oxidation reaction at C-9 by FkbD (P450 hydroxylase) (Motamedi, H. et al., J. Bacteriol. 1996; Shafiee, A. et al., J. Antibiot. 1997).

Recently, the present inventors have established that a post-PKS modification path includes two independent parallel paths via characterization of all FK506 biosynthetic intermediates (Ban, Y. H. et al., J. Nat. Prod. 2013).

In addition to the above immunosuppressive activity, FK506 or derivatives thereof have been reported to have anti-fungal (Nakagawa, H. et al., Clin. Drug Invest. 1996), anti-inflammatory (Migita, K. et al., Curr. Med. Chem. 2003), and neuroprotective and neuroregenerative effects (Gold, B. G. Expert Opin. Invest. Drugs 2000; Gold, B. G. et al., J. Pharmacol. Exp. Ther. 1999). Despite the pharmacological activities above, however, FK506 or derivatives thereof have the immunosuppressive activity, thereby causing a problem such as making it difficult to be used for general patients who require an immune reaction.

DISCLOSURE

Technical Problem

Under such circumstances, intensive research efforts of the present inventors, aimed at ascertaining several features of FK506 involved in the pathway after the PKS deformation resulted in confirmation of a method of producing 9-deoxo-prolyl-FK506 (9-deoxo-prolyl-FK506), a novel FK506 derivative, by inactivation of the FK506 biosynthesis gene and finding that an FK506 derivative which is 9-deoxo-prolyl-FK506, 31-O-demethyl-FK506 (31-O-demethyl-FK506), or 9-deoxo-31-O-demethyl FK506 (9-deoxo-31-O-demethyl-FK506) has reduced immunosuppressive activity and has neuroregenerative and protective effects, and thus can be used for treating nervous system diseases.

Technical Solution

A main object of the present invention is to provide a pharmaceutical composition for preventing or treating nervous system diseases, comprising one or more FK506 derivatives selected from the group consisting of 31-O-demethyl-FK506, 9-deoxo-31-O-demethyl-FK506, or 9-deoxo-prolyl-FK506, with reduced immunosuppressive activity.

Another object of the present invention is to provide a method of preparing 9-deoxo-prolyl-FK506, including a step of culturing a *Streptomyces* strain in which fkbD gene is inactivated.

Still another object of the present invention is to provide 9-deoxo-prolyl-FK506, an isomer thereof or pharmaceutically acceptable salt.

Still another object of the present invention is to provide a composition for promoting neuroregeneration, with reduced immunosuppressive activity, comprising one or more FK506 derivatives selected from the group comprising 31-O-demethyl-FK506, 9-deoxo-31-O-demethyl-FK506, or 9-deoxo-prolyl-FK506.

Advantageous Effects of the Invention

The composition according to the present invention, comprising 9-deoxo-prolyl-FK506, 31-O-demethyl-FK506, or 9-deoxo-31-O-demethyl-FK506, can promote neuroregeneration and reduce side effects in the treatment of nervous system diseases with reduced immunosuppressive activity.

BRIEF DESCRIPTION OF THE DRAWINGS

FIG. 3A is a $^1$H NMR spectrum and FIG. 3B is a $^{13}$C NMR spectrum.

FIG. 5A shows COSY and main HMBC correlations of the above compounds, FIG. 5B shows a COSY spectrum of 9-deoxo-prolyl-FK506 dissolved in CDCl$_3$, and FIG. 5C shows an HMBC spectrum of 9-deoxo-prolyl-FK506 dissolved in CDCl$_3$.

BEST MODE

Figure 1:
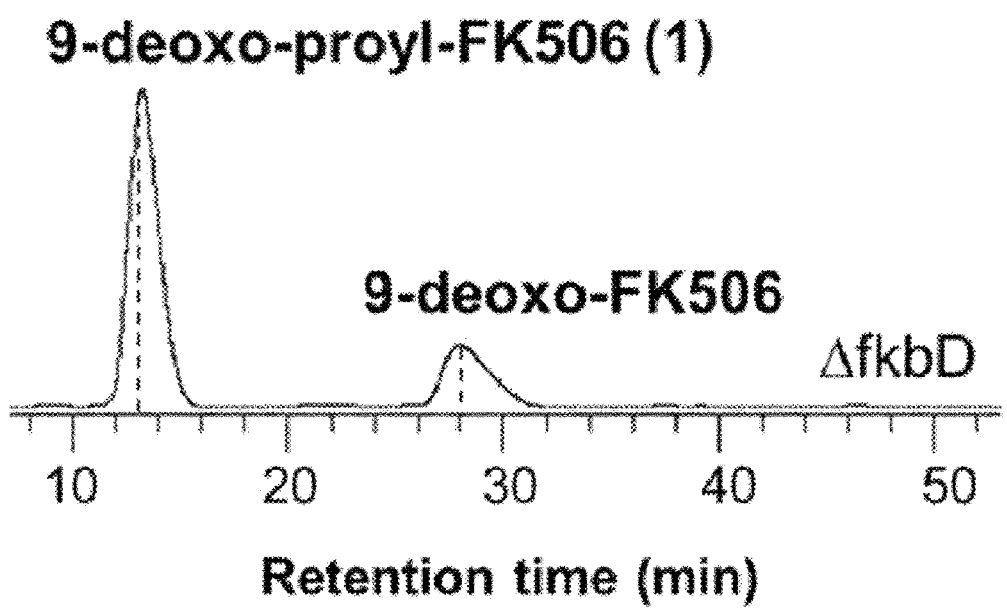
FIG. 1 is a graph showing the result of HPLC ESI-MS analysis of 9-deoxo-prolyl-FK506 obtained from strains (ΔfkbD$_{in\text{-}frame}$) inactivated by an in-frame deletion of fkbD gene.

To achieve the above object, in an aspect, the present invention provides 9-deoxo-prolyl-FK506 represented by Formula 2, which is a novel derivative of FK506 represented by Formula 1, an isomer thereof, or a pharmaceutically acceptable salt thereof.

[Formula 1]

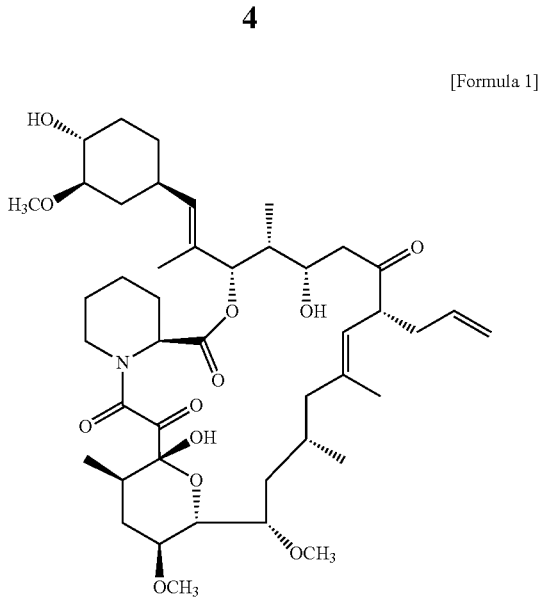

[Formula 2]

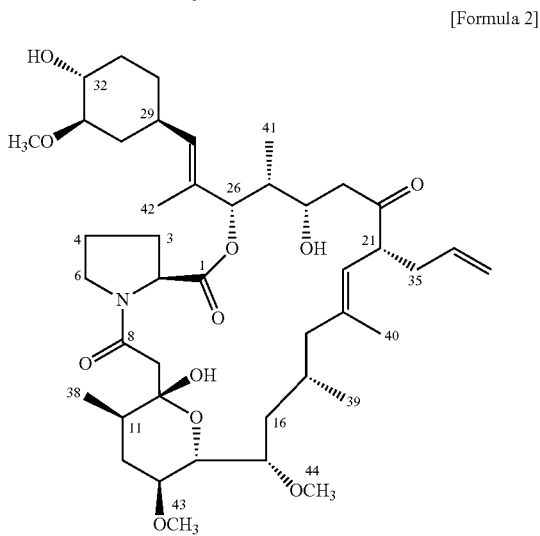

To achieve the above object, in another aspect, the present invention provides a method for preparing 9-deoxo-prolyl-FK506.

As an embodiment, the above preparation method may include a step of culturing a *Streptomyces* strain in which fkbD (P450 hydroxylase) gene is deleted. It is known that the FkbD enzyme which acts in the post-PKS modification causes an oxidation reaction at C-9, but relevance of the FkbD enzyme to the prolyl group has never been reported.

As another embodiment, the above preparation method may include the further step of distributing a supernatant liquid obtained by centrifuging a culture solution of fkbD gene-deleted strain using ethyl acetate and segmenting by preparative reversed-phase HPLC using 60% aqueous methanol. As another embodiment, a step of semi-preparative reversed-phase HPLC using 50% acetonitrile may be further included after the segmentation step.

Additionally, the strain for preparing 9-deoxo-prolyl-FK506 may be a strain of *Streptomyces* capable of producing FK506 inside of the organism. For example, the strain may be selected from the group consisting of *Streptomyces* sp. KCTC11604BP, *Streptomyces kanamyceticus* KCTC9225, *Streptomyces* sp. ATCC55098, *Streptomyces tsukubaensis* No. 9993, *Streptomyces* sp. ATCC53770, *Streptomyces* sp.

6260, *Streptomyces* sp. 49 A, *Streptomyces* sp. 94128, *Streptomyces glaucescens* MTCC5115, and *Streptomyces* sp. BICC7522, but is not limited thereto as long as FK506 can be produced.

The strain may be cultured in a medium containing a nutrient source which microorganisms may utilize. As the nutrient source of the strain, a conventional nutrient source in the art, e.g., a medium containing a malonic acid, ethanol, methionine, and a carbon and nitrogen source, may be used without limitation.

The present inventors identified a substance which is prepared inactivating fkbD gene of *Streptomyces* sp. KCTC11604BP through an in-frame deletion generated by a double cross-over homologous recombination, as 9-deoxo-prolyl-FK506, the novel derivative of FK506, using chemicophysical analysis.

Chemicophysical characteristics of the analyzed 9-deoxo-prolyl-FK506 are as follows: (a) amorphous white powder; (b) specific rotation: $[a]^{23}_D$=1.64 (c=0.1, methanol); (c) UV absorption spectrum (methanol): $\lambda_{max}$ is (log e) 227 nm (2.0); (d) IR absorption spectrum (film): $v_{max}$ 3450, 2960, 1750, 1640, 1170, 1050 cm$^{-1}$; (e) $^1$H and $^{13}$C-NMR, see Table 1; (f) (+)-ESI-MS: m/z 793.1 [M+NH$_4$]$^+$; (+)-MS/MS: m/z 776.1, 758.1, 740.1, 547.9; (+)-HR-ESI-MS: m/z 776.4940 [M+H]$^+$; and (g) molecular formula and weight: $C_{43}H_{70}NO_{11}$, 776.4949.

As a specific embodiment, the compound of the present invention may comprise an isomer or pharmaceutically acceptable salt thereof.

Isomer refers to different compounds with the same chemical formula and may include structural isomers, geometric isomers, optical isomers (enantiomers), stereoisomers, or diastereomers of 9-deoxo-prolyl-FK506, as an example.

A pharmaceutically acceptable salt may be any of an organic or inorganic acid addition salt with a concentration relatively nontoxic to a patient, a harmless effective action, and a side effect which does not reduce the beneficial effects of 9-deoxo-prolyl-FK506. For example, the salt may be an acid addition salt formed by a pharmaceutically acceptable free acid. The acid addition salt may be prepared by a conventional method, i.e., dissolving a compound in an excess amount of an aqueous acid solution and precipitating the salt using a water-miscible organic solvent such as methanol, ethanol, acetone, or acetonitrile. The salt may be also prepared by heating an aqueous acid or alcohol (e.g., glycol monomethyl ether) and the equimolar compounds and then drying the compound by evaporating or suction filtering the precipitated salt. An organic or inorganic acid may be used as the free acid. The pharmaceutically acceptable salt may be a pharmaceutically acceptable metal salt prepared using a base.

As another specific embodiment, the compound of the present invention may be in a form of a solvate or pro-drug which lies within the scope of the present invention. The solvate may preferably include a hydrate or ethanol solvate.

The compound of the present invention may be synthesized according to a conventional method in the art. For example, the compound may be produced from a variant using the preparation method of the present invention.

To achieve the above object, in another aspect, the present invention provides a pharmaceutical composition for preventing or treating nervous system diseases, comprising one FK506 derivative selected from the group consisting of 9-deoxo-prolyl-FK506, 31-O-demethyl-FK506 represented by Formula 3 below, and 9-deoxo-31-O-demethyl-FK506 represented by Formula 4 below.

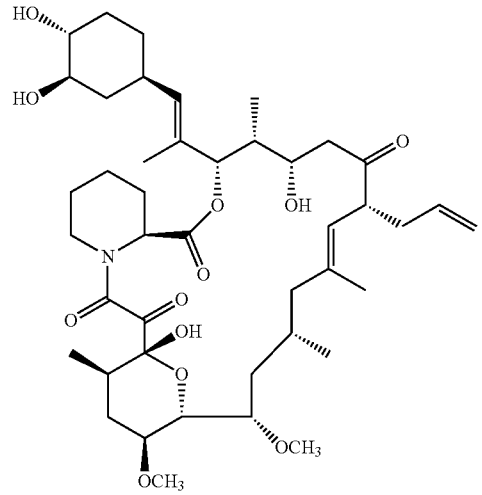

[Formula 3]

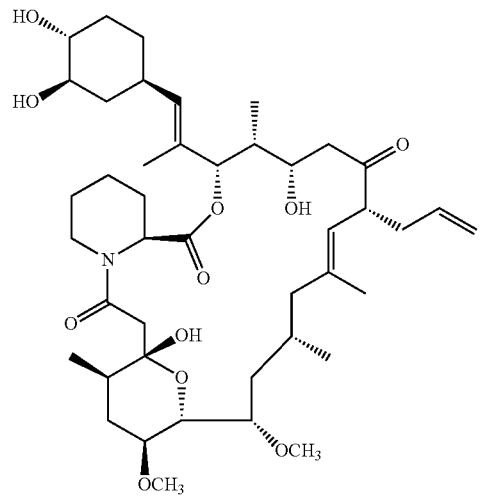

[Formula 4]

Since FK506 is an important enzyme in T-cell receptor signaling and inhibits the activity of calcineurin which suppresses T lymphocyte activity, it is used as an immunosuppressant for clinically preventing allograft rejection and treating autoimmune diseases such as atopy. In addition to the immunosuppressive activity, FK506 has been reported to have antifungal, anti-inflammatory, neuroprotective, and neuroregenerative effects. However, despite the pharmacological activities, there is a problem such as making it difficult to use for general patients who require an immune reaction due to the immunosuppressive activity.

As a result of treating CD3/CD28-activated human T-cells with 9-deoxo-prolyl-FK506, 31-O-demethyl-FK506, or 9-deoxo-31-O-demethyl-FK506, the present inventors confirmed that the secretion of interleukin-2 increased significantly to reach a normal level. The FK506 derivative was also confirmed to show an excellent neuroregenerative activity. Accordingly, the pharmaceutical composition according to the present invention may show a therapeutic effect on nervous system diseases without the immunosuppressive activity.

As an embodiment, the nervous system diseases may be neurodegenerative diseases. The neurodegenerative diseases refer to diseases characterized by degenerative changes in neurons of the central nervous system, causing several symptoms, e.g., dementia, Alzheimer's disease, Parkinson's disease, progressive supranuclear palsy, multiple system atrophy, olivopontocerebellar atrophy (OPCA), Shy-Drager syndrome: striatonigral degeneration, Huntington's disease, amyotrophic lateral sclerosis (ALS), essential tremor, corticobasal ganglionic degeneration, diffuse Lewy body disease, Parkinson-ALS-dementia complex of Guam, or Pick's disease.

As another embodiment, the nervous system diseases may include epilepsy, paralysis, stroke, ischemic brain disease, spinal cord injury disease, peripheral nerve disease, behavioral disorder, developmental disorder, mental retardation, Down's syndrome, or schizophrenia, but are not limited thereto.

As another embodiment, the nervous system diseases may be a disease caused by neuronal damage or cell death.

The present inventors confirmed that 9-deoxo-prolyl-FK506, 31-O-demethyl-FK506, or 9-deoxo-31-O-demethyl-FK506 promotes neurite outgrowth in PC12 cells and induces neuroregeneration, and thus can be used for promoting neuroregeneration or for preventing or treating nervous system diseases.

As used herein, the term "prevent" may refer to all actions of suppressing or of delaying the onset of nervous system diseases by administering the composition for preventing or treating nervous system diseases according to the present invention to a subject.

As used herein, the term "treat" may refer to all actions of improving or of alleviating symptoms of nervous system diseases by administering the composition of the present invention to a subject suspected of developing a nervous system disorder.

The pharmaceutical composition of the present invention may be used as a single formulation or a combined formulation prepared by additionally containing a drug, which is publicly known to have a therapeutic effect on neuronal diseases, in a unit dose form formulated using a pharmaceutically acceptable carrier or excipient, or encapsulated into a multi-dose container.

As used herein, the term "pharmaceutically acceptable carrier" may refer to a carrier or diluent which does not inhibit biological activities and properties of a compound to be introduced to a subject without irritating the subject. A type of the carrier which may be used in the present invention is not particularly limited, and any carrier may be used as long as it is a pharmaceutically acceptable carrier commonly used in the art. Non-limiting examples of the carriers may include physiological saline, sterile water, Ringer's solution, buffered saline, albumin injection solution, dextrose solution, maltodextrin solution, glycerol, and ethanol. The carriers may be used independently or in a combination of two or more, and may include a non-naturally occurring carrier.

Additionally, if necessary, other conventional additives such as an antioxidant, buffer, and/or bacteriostatic agent may be added, and a diluent, dispersant, surfactant, binder, or lubricant may be further added to be used in an injectable formulation such as an aqueous solution, suspension, and emulsion; pill; capsule; granule; or tablet.

Additionally, the pharmaceutical composition of the present invention may contain a pharmaceutically effective amount of 9-deoxo-prolyl-FK506, 31-O-demethyl-FK506, or 9-deoxo-31-O-demethyl-FK506. As used herein, the term "pharmaceutically effective amount" refers to an amount sufficient to treat a disease at a reasonable benefit/risk ratio applicable to medical treatment, and the compound may be generally administered in an amount of from 0.001 to 1000 mg/kg, preferably 0.05 to 200 mg/kg, more preferably 0.1 to 100 mg/kg in a single or multiple doses per day. For the purpose of the present invention, however, it is preferable that a specific therapeutically effective amount for a particular patient is administered depending upon a type and degree of a desired reaction, whether other formulations are used in some cases, a specific composition, age, body weight, general health condition, sex, diet, time and route of administration, secretion rate of a composition, period of treatment, and drug used either simultaneously or in combination with a specific composition, and other various factors and similar factors well-known in the pharmaceutical field.

The pharmaceutical composition of the present invention may be administered as an independent therapeutic agent or in combination with other therapeutic agents, and sequentially or simultaneously with conventional therapeutic agents. The pharmaceutical composition of the present invention may be administered as a single or multi-dose. It is important that administration be performed in light of all the above-described factors so that a maximum effect may be obtained with a minimum amount without any side effects, and the composition may be easily determined by one of ordinary skill in the art.

As used herein, the term "administration" refers to an introduction of the pharmaceutical composition of the present invention to a patient in an appropriate manner. The composition of the present invention may be administered by an oral or various parenteral routes capable of delivery of the composition to a target tissue.

The method of administering the pharmaceutical composition according to the present invention is not particularly limited, and may follow a method conventionally used in the art. As a non-limiting example of the administration method, the composition may be administered in an oral or parenteral route. The pharmaceutical composition according to the present invention may be formulated in various dosage forms depending on an intended administration method.

The pharmaceutical composition of the present invention may be, for example, administered in an amount of 1 to 20 mg/kg, preferably 1 to 10 mg/kg to mammals including humans. An administration frequency of the composition is not particularly limited, and may be once or several times per day.

As another aspect for achieving the above object, the present invention provides a composition for promoting neuroregeneration with reduced immunosuppressive activity, comprising one or more FK506 derivatives selected from the group consisting of 31-O-demethyl-FK506, 9-deoxo-31-O-demethyl-FK506, and 9-deoxo-prolyl-FK506.

As an example, the composition may be used as a composition which promotes in vitro neurite outgrowth.

To achieve the above object, in another aspect, the present invention provides a method for preventing or treating a nervous system disease, including a step of administering a composition for accelerating neuroregeneration to a subject.

As used herein, the term "subject" may refer to all animals including humans wherein a nervous system disease has been developed or may be developed. The animals may be not only humans but also cattle, horses, sheep, pigs, goats, camels, antelope, dogs, cats, and other mammals which need treatment of a similar symptom, but are not limited thereto.

The prophylactic or therapeutic method of the present invention may specifically include a step of administering the composition in a pharmaceutically effective amount to a subject at a risk of having developed or developing a nervous system disease.

As used herein, the term "administration" refers to introducing the pharmaceutical composition of the present invention into a patient in any appropriate manner, and as long as the composition can be delivered to a target tissue, the composition can be administered by oral or various parenteral routes.

DETAILED DESCRIPTION OF THE INVENTION

Hereinafter, the present invention will be described in more detail with reference to the following Examples. However, these Examples are for illustrative purposes only, and the invention is not intended to be limited by these Examples.

Example 1. Material Preparation Method and Conditions (1) Construction of Variant and Culture Conditions $\Delta fkbD_{in-frame}$ strain was prepared by inactivating fkbD gene of *Streptomyces* sp. KCTC11604BP through an in-frame deletion generated by a double cross-over homologous recombination, according to the preparation method Ban, Y. H. et al. disclosed (J. Nat. Prod. 2013, 76, 1091-1098).

Spores of the KCTC11604BP strain and the fkbD gene-deleted $\Delta fkbD_{in-frame}$ were subcultured on ISP4-agar plates, and seed cultures were prepared in an R2YE medium. 50 mg of vegetative cells grown in the seed cultures for six days were inoculated into 50 mL of the R2YE medium contained in a 250 mL baffled flask and then incubated in an orbital shaker (fixed at 180 rpm) at 28° C. for 6 days.

(2) Extraction and Isolation

4 L of culture broth of the $\Delta fkbD_{in-frame}$ strain was centrifuged, and the supernatant was subjected to solvent-solvent partitioning twice using ethyl acetate. The layer dissolved in ethyl acetate was isolated and evaporated under reduced pressure to yield a dark red extract. The extract was fractionated by preparative reversed-phase HPLC using 60% aqueous methanol as mobile phase with a flow rate of 2 mL/min, and then HPLC-ESI-MS analysis was performed.

HPLC-ESI-MS/MS spectra using an ACQUITY UPLC BEH C18 column (50×2.1 mm, 1.7 μm; Waters) were recorded on a Waters/Micromass Quattro micro MS interface consisting of a Waters 2695 separation module directly connected to a Micromass Quattro micro MS.

Tracing was carried out by MS/MS operated in multiple reaction monitoring mode in which a mass pair specific to a selected analyte is selected, in order to detect a transition from a parent ion such as an ammonium adduct to a product ion.

In order to separate the fraction into two subfractions, semipreparative reversed-phase HPLC was further carried out with a flow rate of 2 mL/min and 50% aqueous acetonitrile as a mobile phase. As a result of purifying the subfractions under the same column and HPLC conditions, an amorphous white powder (7.4 mg, $t_R$ 90 min) was obtained.

(3) Method of Data Measurement

Optical rotation was measured with a Jasco P-1010 polarimeter using a cell with a 0.1 dm path length.

UV spectra were recorded with a Scinco S-3100 spectrophotometer, and IR spectra were obtained on a Varian FTS-800 FTIR spectrometer.

NMR spectra were recorded using a Varian INOVA 500 spectrometer ($^{13}$C, 125 MHz) operating at 500 MHz for 1 hour. Chemical shifts were expressed in ppm using tetramethylsilane (TMS) as an internal reference. Mnova Software (Mestrelab Research S.L.) was used for processing all NMR data. Samples for NMR analysis were prepared by dissolving the pure compound in 250 μL of CDCl$_3$ (Sigma) and then placing the solution in a 5 mm Shigemi Advanced NMR microtube (Sigma) corresponding to the solvent.

HR-ESI-MS data was collected using a Waters SYNAPT G2 mass spectrometer coupled with UPLC. HPLC purification was performed using a semiseparation Watchers 120 ODS-BP (250×10 mm, 5 μm) on an Acme 9000 HPLC system (YL Instrument Co. Ltd., Korea) consisting of a SP930D gradient pump connected with a UV 730 D UV detector set (205 nm) and CTS 30 column oven set (50° C.). The HPLC grade solvents used for the experiment were purchased from J. T. Baker.

Example 2. Observation of the Results of Example 1

The result of the amorphous white solid analysis is as follows.

(1) HPLC-ESI-MS

Figure 2:
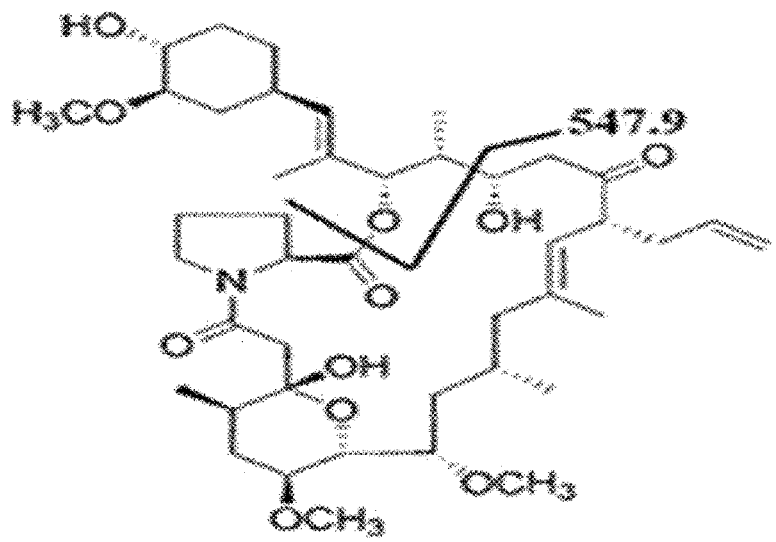
FIG. 2 is the result of ESI-MS/MS analysis of 9-deoxo-prolyl-FK506, where (A) shows a pattern of ESI-MS/MS fragments and (B) shows an MS/MS spectrum.
Figure 2:
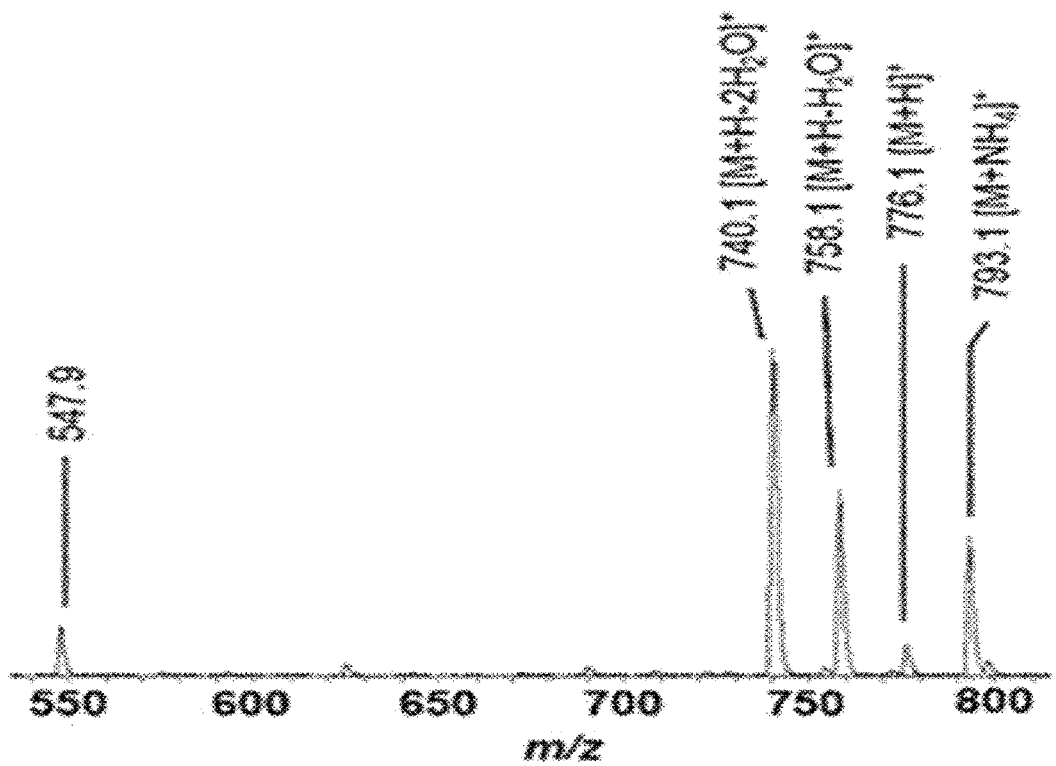

FIG. 1 is a result of HPLC-ESI-MS analysis of the culture extract of $\Delta fkbD_{in-frame}$ strain, where ammonium adduct ion peaks eluted at 13 minutes with m/z 793.1 and at 28 minutes with m/z 807.1. Accordingly, the peak eluted at 13 minutes with m/z 793.1 was predicted to be 9-deoxo-prolyl-FK506 based on the fragment ions at 776.1, 758.1, 740.1, and 547.9 as shown in FIG. 2. The fragmentation pattern of 9-deoxo-prolyl-FK506 was similar to that of 9-deoxo-FK506 in that the distance between each of the fragment ions is 14 Da. The characteristic C-1-C-24 fragment ion appeared at m/z 561.9 in 9-deoxo-FK506 whereas the same for 9-deoxo-prolyl-FK506 of the present invention was denoted by an ion peak with m/z 547.9. This implies that 9-deoxo-prolyl-FK506 has one less methylene group in the characteristic C-1-C-24 fragment than 9-deoxo-FK506 and other 9-deoxo-FK506 derivatives.

Therefore, the amorphous white solid, that is 9-deoxo-prolyl-FK506, was assumed to contain a proline.

(2) 1D- and 2D-NMR

TABLE 1

| | | 1D- and 2D-NMR Data | | |
|---|---|---|---|---|
| Location | $\delta_C$ | $\delta_H$, m (J in Hz) | $^1$H-$^1$H COSY | HMBC |
| 1 | 169.9 | | | |
| 2 | 58.9 | 4.35, dd (8, 3) | H-3a, H-3b | C-1, C-3, C-4, C-6 |
| 3 | 29.2 | 2.19, m | H-2, H-4 | C-1, C-2, C-4, C-6 |
| | | 1.98, m | H-2 | C-1, C-2, C-6 |
| 4 | 24.7 | 1.96, m | H-6a, H-6b, H-3a | C-3, C-6 |
| 5 | | | | |
| 6 | 47.4 | 3.63, m | H-4 | C-2, C-3, C-4 C-2, |
| | | 3.54, m | H-4 | C-3, C-4 |
| 7 | | | | |
| 8 | 171.8 | | | |
| 9 | 39.2 | 2.64, d (15) | H-9b | C-8, C-10 |
| | | 2.56, d (15) | H-9a | C-8, C-10 |
| 10 | 98.6 | | | |
| 11 | 38.6 | 1.61, m | H-12a, H-38 | C-10 |

TABLE 1-continued 1D- and 2D-NMR Data

| Location | $\delta_C$ | $\delta_H$, m (J in Hz) | $^1$H-$^1$H COSY | HMBC |
|---|---|---|---|---|
| 12 | 32.7 | 1.99, m | H-11, H-13 | C-10, C-13, C-14, C-38 |
|  |  | 1.55, m | H-13 | C-10, C-13, C-38 |
| 13 | 74.6 | 3.40, (overlapped) | H-12a, H-12b, H-14 | C-14, C-43 |
| 14 | 71.0 | 3.84, dd (10, 2.5) | H-13, H-15 | C-10, C-12, C-13 |
| 15 | 77.1 | 3.53, m | H-14, H-16a, H-16b |  |
| 16 | 36.4 | 1.46, m | H-15 H-15, H-17 | C-17, C-19 |
|  |  | 1.35, m |  | C-17, C-19 |
| 17 | 25.6 | 1.61, (overlapped) | H-39, H-16b, H-18a |  |
| 18 | 49.0 | 2.33, m | H-17 | C-17, C-19, C-20, C-39 |
|  |  | 1.69, m |  |  |
| 19 | 141.1 |  |  |  |
| 20 | 121.9 | 5.01, overlapped | H-21 | C-18, C-21, C-22, C-40 |
| 21 | 53.4 | 3.36, overlapped | H-20, H-35a, H-35b | C-22, C-20, C-35, C-36 |
| 22 | 214.0$^a$ |  |  |  |
| 23 | 44.0 | 2.69, dd (17, 2) | H-23b H-23a, H-24 | C-22, C-24 |
|  |  | 2.34, dd (17, 7) |  | C-22, C-24, C-25 |
| 24 | 69.1 | 4.02, dd (7, 3) | H-23b, H-25 | C-22, C-26, C-41 |
| 25 | 41.2 | 1.81, m (3) | H-24, H-26, H-41 |  |
| 26 | 78.0 | 5.17, d (2.5) | H-25 | C-1, C-24, C-25, C-27, C-28, C-41, C-42 |
| 27 | 132.4 |  |  |  |
| 28 | 129.7 | 4.98, (overlapped) | H-29 | C-26, C-27, C-29, C-30, C-34, C-42 |
| 29 | 35.0 | 2.27, m | H-28, H-30a, H-30b, H-34a, H-34b | C-30 |
| 30 | 34.9 | 2.05, m | H-29, H-30b, H-31 H-29, H-30a, H-31 | C-31 C-31 |
|  |  | 0.97, (overlapped) |  |  |
| 31 | 84.4 | 2.99, ddd (8.5, 4.5, 2.5) | H-30a, H-30b, H-32 | C-32, C-45 |
| 32 | 73.7 | 3.40, (overlapped) | H-31, H-33a, H-33b |  |
| 33 | 31.4 | 1.98, m | H-32, H-33b, H-34a, H-34b H-32, H-33a, H-34a, H-34b |  |
|  |  | 1.35, m |  |  |
| 34 | 30.8 | 1.61, m | H-29, H-33a, H-33b, H-34b H-29, H-33a, H-33b, H-34a |  |
|  |  | 1.04, m |  |  |
| 35 | 35.7 | 2.45, m (7) | H-36, H-21 | C-20, C-21, C-22, C-36, C-37 C-20, C-21, C-22, C-36, C-37 |
|  |  | 2.25, m | H-36, H-21 |  |
| 36 | 135.6 | 5.70, ddt (17, 10, 7) | H-35a, H-35b, H-37 | C-21, C-35 |
| 37 | 116.7 | 5.00, br s | H-36 | C-35, C-36 |
| 38 | 17.1 | 0.95, d (6.5) | H-11 | C-10, C-11, C-12 |
| 39 | 19.0 | 0.75, d (6.5) | H-17 | C-16, C-17, C-18 |
| 40 | 15.7 | 1.67$^b$, s |  | C-19, C-20 |
| 41 | 10.0 | 0.90, d (6.5) | H-25 | C-24, C-25, C-26 |
| 42 | 14.4 | 1.66$^b$, s |  | C-27, C-28 |
| 43 | 56.3 | 3.37$^b$, s |  | C-13 |
| 44 | 57.8 | 3.36$^b$, s |  | C-15 |
| 45 | 56.7 | 3.40, s |  | C-31 |
| 10-OH |  | 6.76, s |  | C-8, C-9 |

Figure 3A:
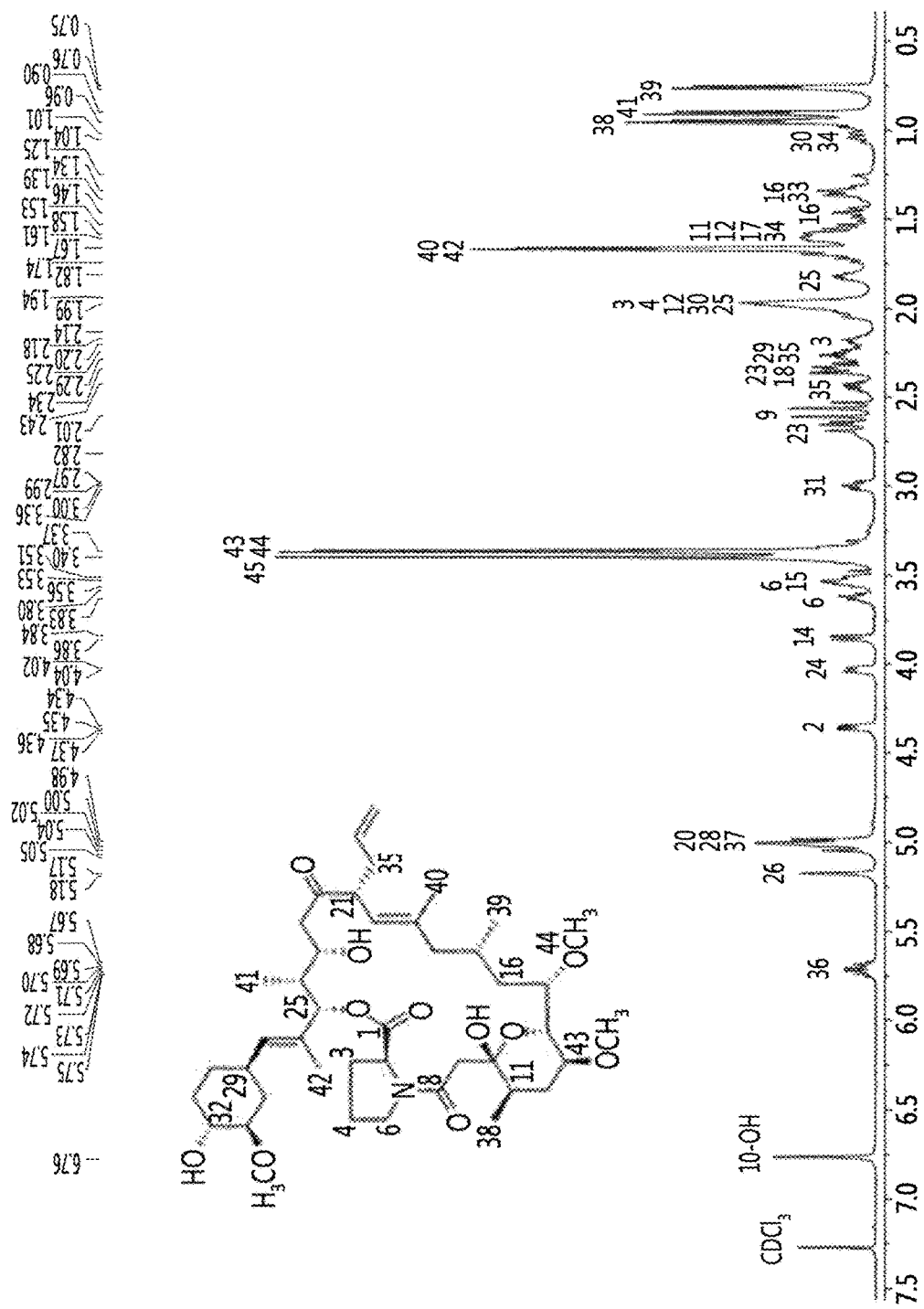
FIGS. 3A and 3B are NMR spectra of 9-deoxo-prolyl-FK506 dissolved in CDCl$_3$, where

As shown in Table 1 above and FIG. 3a, as a result of $^1$H NMR spectrum analysis, characteristic signals of the FK506 skeleton were observed: three doublets corresponding to methyl groups ($\delta_H$ 0.95/H$_3$-38, 0.90/H$_3$-41, and 0.75/H$_3$-39); two methyl singlets ($\delta_H$ 1.67/H3-40 and 1.66/H3-42); three methoxy singlets ($\delta_H$ 3.40/H3-45, 3.37/H3-43, and 3.36/H3-44); and a multiplet of an olefinic proton ($\delta_H$ 5.70/H-36).

Figure 3B:
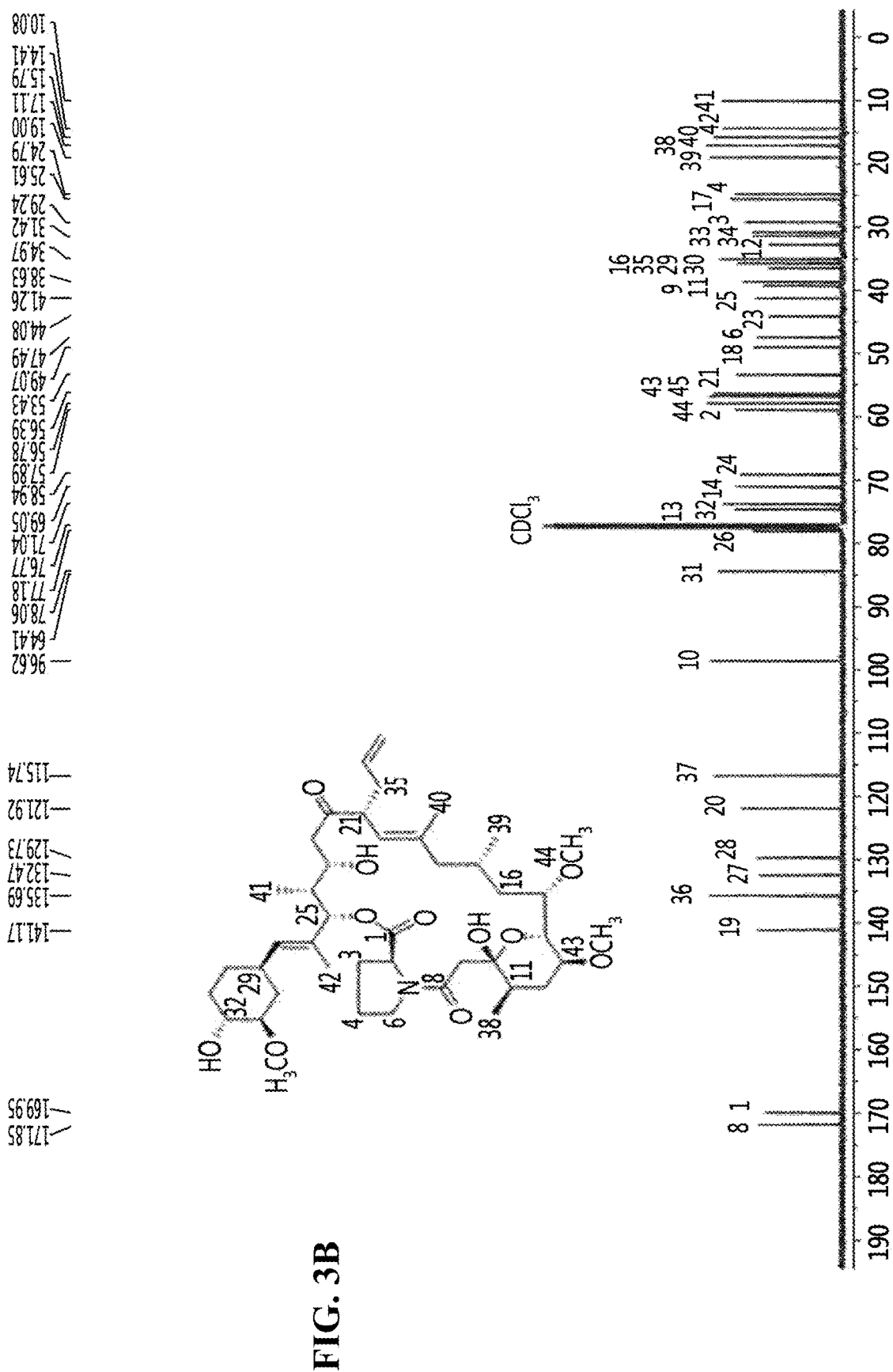

Additionally, as shown in FIG. 3b, as a result of $^{13}$C NMR spectrum analysis, the compound are expected to have 43 carbons in total, considering 42 carbon signals from the $^{13}$C NMR spectrum and one carbonyl carbon from the HMBC spectrum. However, a careful comparison of the NMR data of the compound (9-deoxo-prolyl-FK506) to that of 9-deoxo-FK506 indicated that the signals of the compound corresponding to the pipecolate moiety (C-2-C-6) of 9-deoxo-FK506 shifted.

Figure 4:
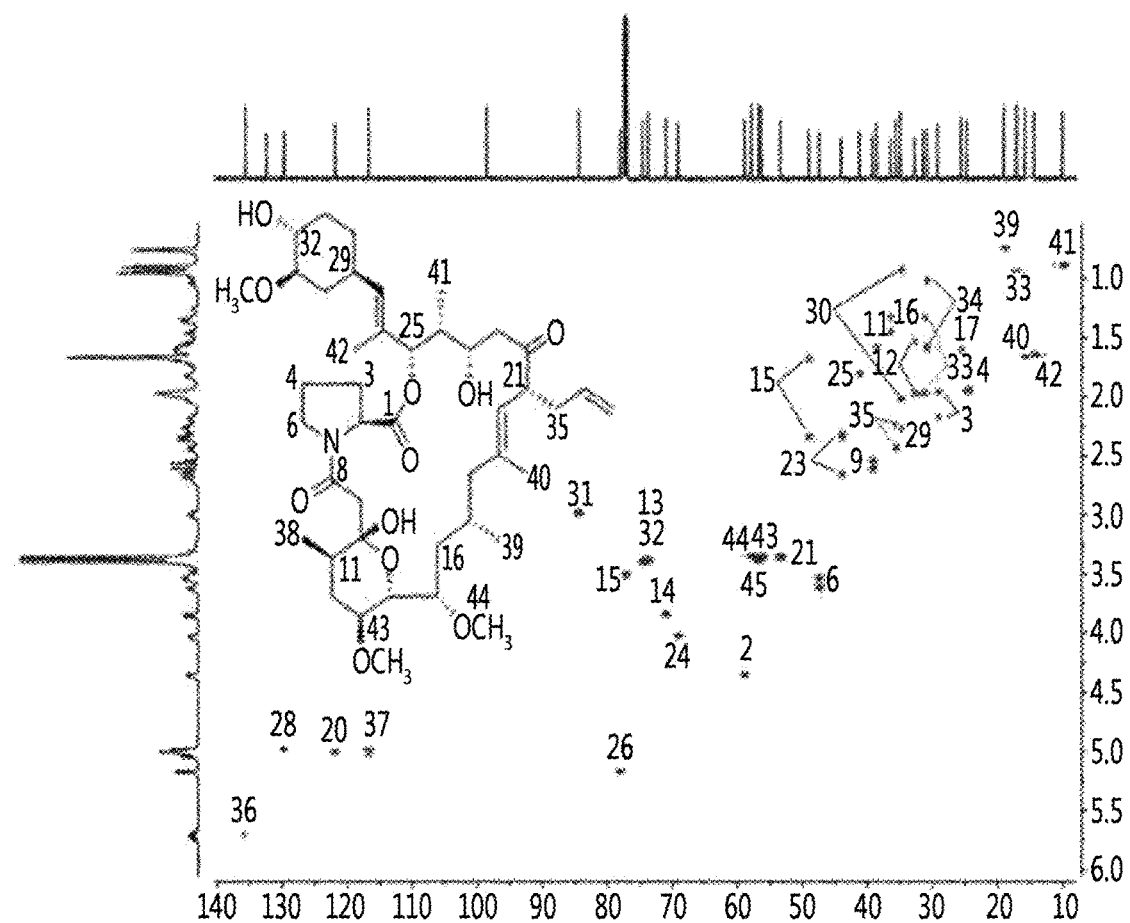
FIG. 4 is an HSQC spectrum of 9-deoxo-prolyl-FK506 dissolved in CDCl$_3$.

Further, analysis of the obtained $^1$H and $^{13}$C spectra above and HSQC spectra of the compound in FIG. 4 showed 4 carbon signals at $\delta_C$ 58.9/C-2 ($\delta_H$ 4.35/H-2), 47.4/C-6 ($\delta_H$ 3.63/H-6a, 3.54/H-6b), 29.2/C-3 ($\delta_H$ 2.19/H-3a, 1.98/H-3b), and 24.7/C-4 ($\delta_H$ 1.96/H2-4), confirming the presence of the proline moiety in the compound, rather than pipecolate.

Figure 5A:
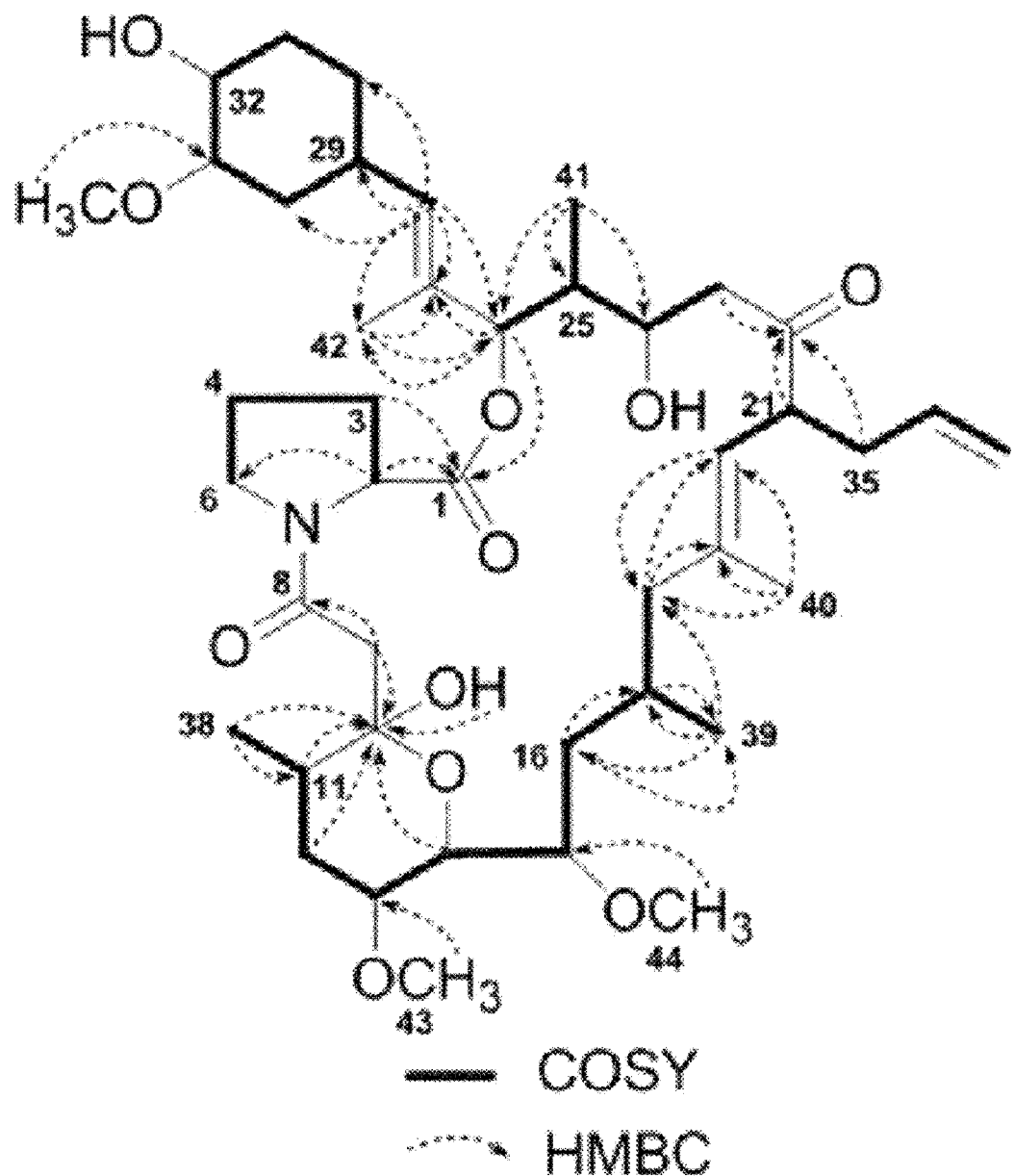
FIGS. 5A to 5C are results of COSY and HMBC analysis of 9-deoxo-prolyl-FK506, where
Figure 5B:
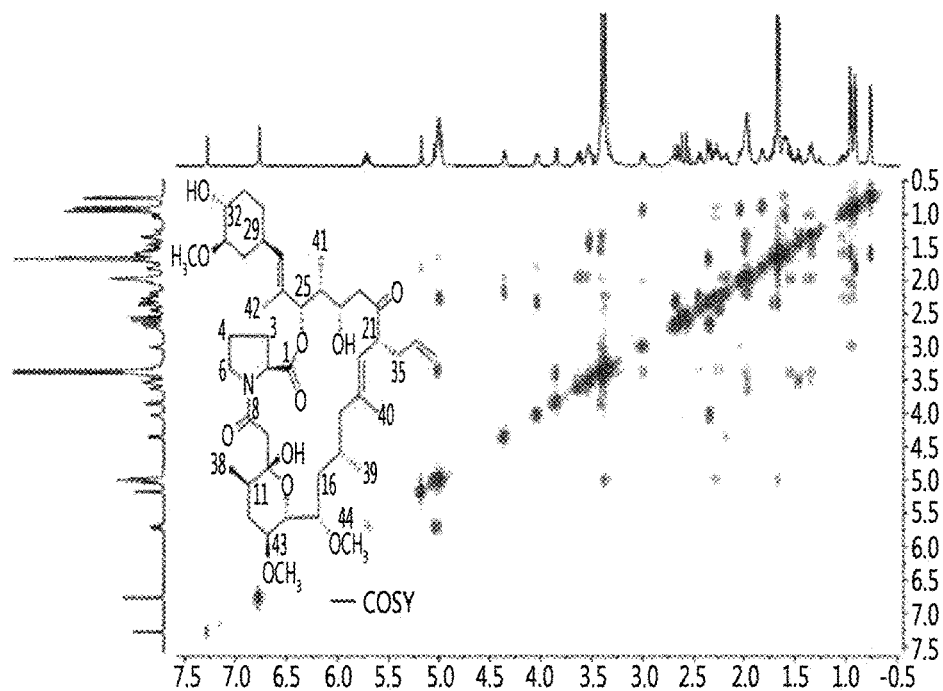
Figure 5C:
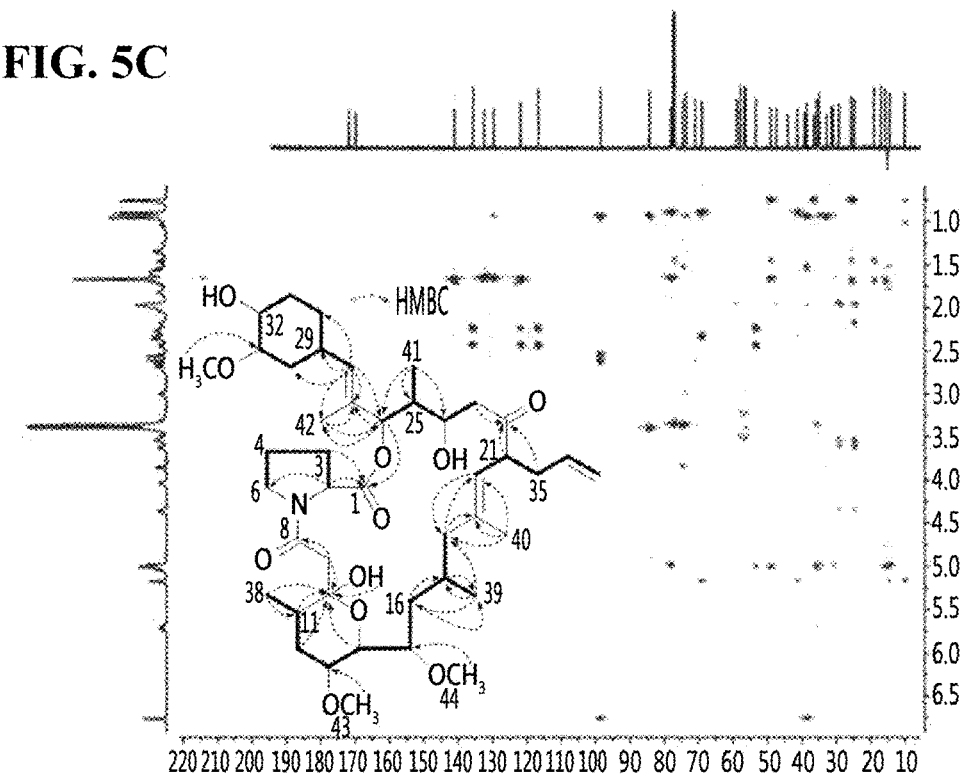

The presence of the proline moiety of the compound was confirmed through COSY and HMBC analysis as shown in FIGS. 5a to 5c. The COSY crosspeaks in the range of $\delta_H$ 4.35 to $\delta_H$ 3.54 provided H-2/H-3/H-4/H-6 connectivity. Furthermore, the key HMBC correlations between the proton signals at $\delta_H$ 4.35/H-2, 2.19/H-3a, and 1.98/H-3b and the carbonyl ester carbon signal at $\delta_C$ 169.9/C-1, as well as proton signals at $\delta_H$ 3.63/H-6a and 3.54/H-6b and the carbon signals at $\delta_C$ 58.9/C-2 and 29.2/C-3 were observed.

The HSQC spectrum in FIG. 4 shows that the proton signals at $\delta_H$ 2.64 (d, J=15 Hz) and 2.56 (d, J=15 Hz) were correlated with the carbon signal at $\delta_C$ 39.2. These proton signals show HMBC correlations to both C-8 ($\delta_C$ 171.8) and C-10 ($\delta_C$ 98.6) (FIGS. 5a and 5c), indicating that the compound is a 9-deoxo-FK506 derivative similar to 9-deoxo-FK506.

Meanwhile, the COSY spectrum of the compound shows the remaining 4 spin systems, which are connected on the basis of HMBC correlations (FIGS. 5a to 5c). Positions of the methyl and methoxy groups were determined on the basis of the relative HMBC correlations as shown in FIG. 5a.

Therefore, the compound was determined as 9-deoxo-prolyl-FK506, and the present inventors revealed for the first time the 9-deoxo-FK506 derivative containing a proline moiety instead of a common pipecolate ring. Additionally, the stereochemistry of the compound is the same as that of the parent compound, FK506.

(3) HR-ESI-MS

As a result of HR-ESI-MS analysis of the amorphous white solid, an [M+H]$^+$ ion was obtained at m/z 776.4940, which is consistent with a molecular formula $C_{43}H_{70}NO_{11}$ (calculated m/z 776.4949).

(+)-ESI-MS m/z 793.1 [M+NH$_4$]$^+$; (+)-MS/MS: m/z 776.1, 758.1, 740.1, 547.9

(+)-HR-ESI-MS m/z 776.4940 [M+H]$^+$ (calculated for C$_{43}$H$_{70}$NO$_{11}$, 776.4949).

Based on the results above, the amorphous white powder isolated in the culture broth of the strain inactivated by in-frame deletion of the fkbD gene of *Streptomyces* sp. KCTC11604BP has chemicophysical characteristics as follows, and therefore has been identified 9-deoxo-prolyl-FK506.

(a) Amorphous white powder;
(b) Specific rotation: [a]$^{23}_D$=1.64 (c=0.1, methanol);
(c) UV absorption spectrum (methanol): $\lambda_{max}$ (log e) 227 nm (2.0);
(d) IR absorption spectrum (film): $v_{max}$ 3450, 2960, 1750, 1640, 1170, 1050 cm$^{-1}$;
(e) $^1$H- and $^{13}$C-NMR spectra (see Table 1);
(f) (+)-ESI-MS: m/z 793.1 [M+NH$_4$]$^+$;
(+)-MS/MS: m/z 776.1, 758.1, 740.1, 547.9;
(+)-HR-ESI-MS: m/z 776.4940 [M+H]$^+$;
(g) Molecular formula and weight: C$_{43}$H$_{70}$NO$_{11}$, 776.4949.

Example 3. Analysis of 9-Deoxo-Prolyl-FK506 Activity (1) Analysis of In Vitro T-Cell Activity A relative immunosuppressive property of the compound compared to authentic FK506 was determined using T-lymphocytes as described in Mo, S. J. et al. (J. Am. Chem. Soc. 2011, 133, 976-985). Simply, interleukin-2 secretions were quantified after treating the compound (0.1 nM) with CD3/CD28-activated human T-cells with the compounds for 16 to 20 hours.

Figure 6:
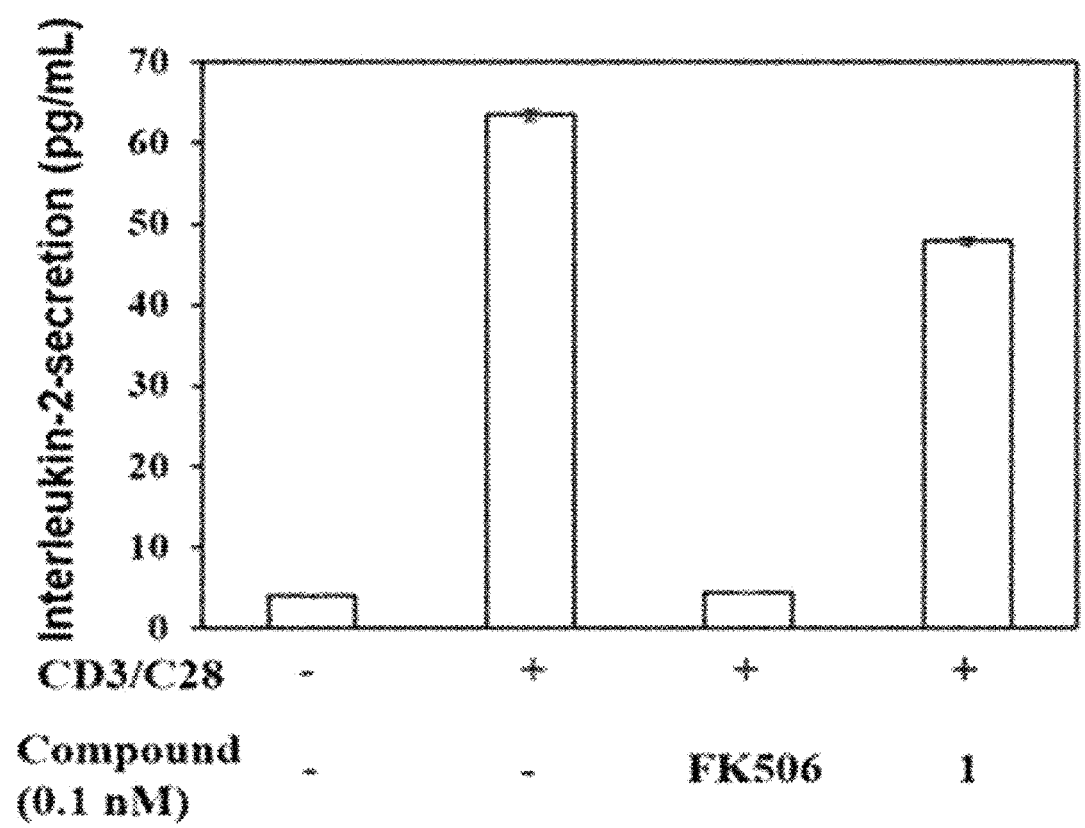
FIG. 6 shows an immunosuppressive activity of 9-deoxo-prolyl-FK506 in comparison with FK506.

As a result, as shown in FIG. 6, when CD3/CD28-activated human T-cells were treated with FK506, the interleukin-2 secretion decreased as much as the number of CD3/CD28-inactivated human T-cells, thereby increasing the immunosuppressive activity. In contrast, when the CD3/CD28-activated human T-cells were treated with 9-deoxo-prolyl-FK506 (marked as 1) according to the present invention, the interleukin-2 secretion significantly increased to reach that of the normal group, indicating a result opposite to the immunosuppressive activity of the parent ion, FK506, and derivatives thereof.

(2) Analysis of Nerve Regeneration Activity

A relative nerve regeneration activity of the compound, compared to authentic FK506, was determined using rat pheochromocytoma cells (PC12) by the method described in Mo, S. J. et al. (J. Am. Chem. Soc. 2011, 133, 976-985). The PC12 cells were treated with nerve growth factor (NGF; KOMA Biotech; 10 ng/mL) which induces neurite outgrowth for 96 hours. 10 nM of FK506 or 9-deoxo-prolyl-FK506 was treated together or excluded. The neurite lengths were measured on photographic prints by the method Revill, W. P. et al. described (J. Pharmacol. Exp. Ther. 2002, 302, 1278-1285).

Figure 7A:
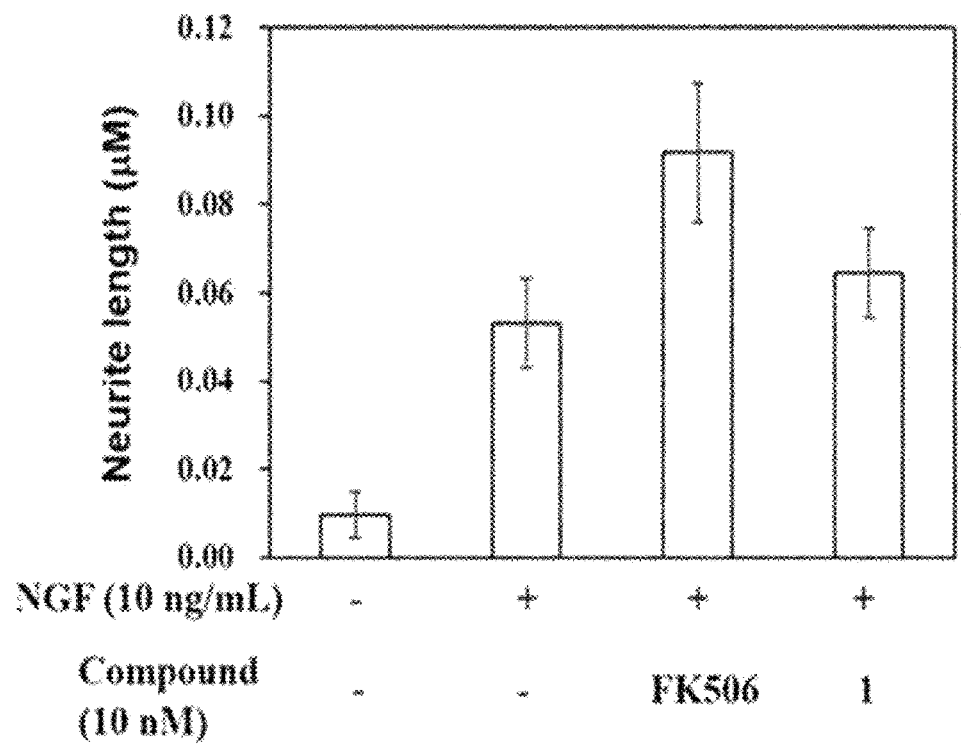
FIG. 7A shows neuroregenerative activity of 9-deoxo-prolyl-FK506, in comparison with FK506.
Figure 7B:
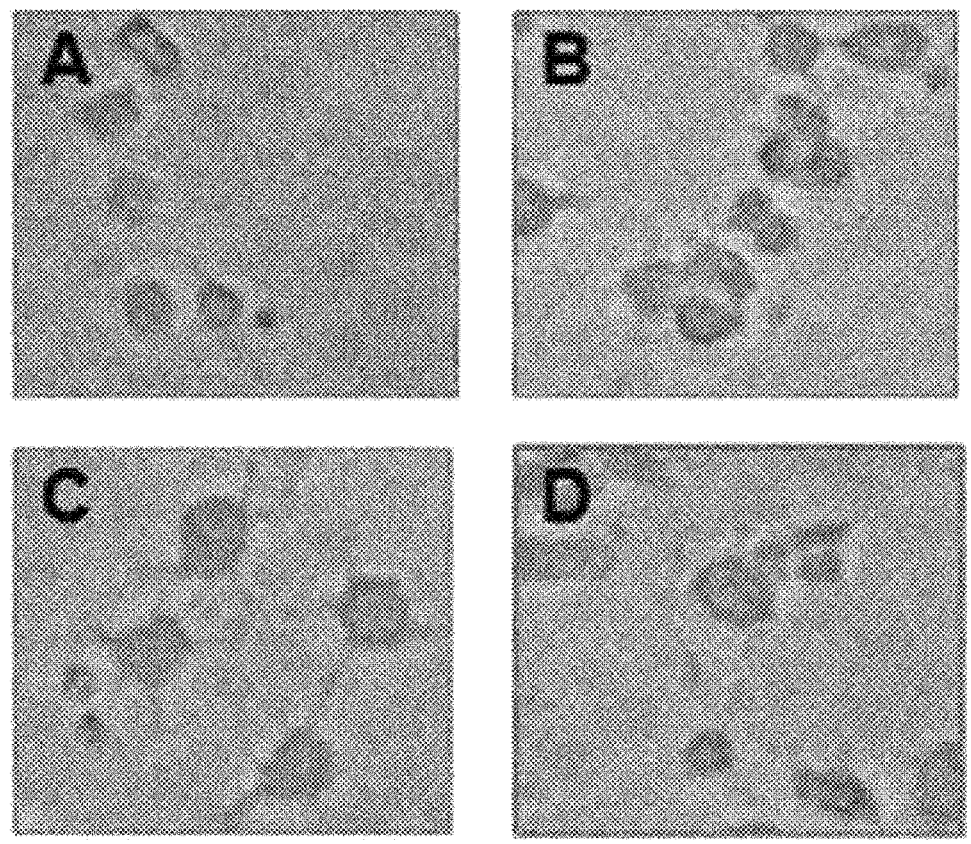
FIG. 7B shows neurites grown on PC12 cells treated with 9-deoxo-prolyl-FK506.

As a result, as shown in FIGS. 7a and 7b, 9-deoxo-prolyl-FK506 (marked as 1) according to the present invention showed an excellent effect on neurite outgrowth promotion. In FIG. 7b, A refers to untreated cells, B refers to cells only treated with nerve growth factor, C refers to cells treated with nerve growth factor in the presence of FK506, and D refers to cells treated with nerve growth factor in the presence of 9-deoxo-prolyl-FK506.

Immunosuppressive and neuroregenerative activities arise via different mechanisms, that is, through either complexes of FKBP12 or FKBP52 (Gold, B. G. Expert Opin. Invest. Drugs 2000, 9, 2331-42). Accordingly, since the loss of immunosuppressive activity due to a reduced ability to form a binary complex with FKBP12 does not inhibit the formation of FKBP52 complexes, the neuroregenerative activity can be maintained. This applies to 31-O-demethyl-FK506 and 9-deoxo-31-O-demethyl-FK506 below in the same manner.

Example 4. Analysis of 31-O-Demethyl-FK506 Activity (1) Analysis of In Vitro Activity of T-Cells A relative immunosuppressive property of 31-O-demethyl-FK506 compared to authentic FK506 was determined using the same method as Example 3. (1).

Figure 8:
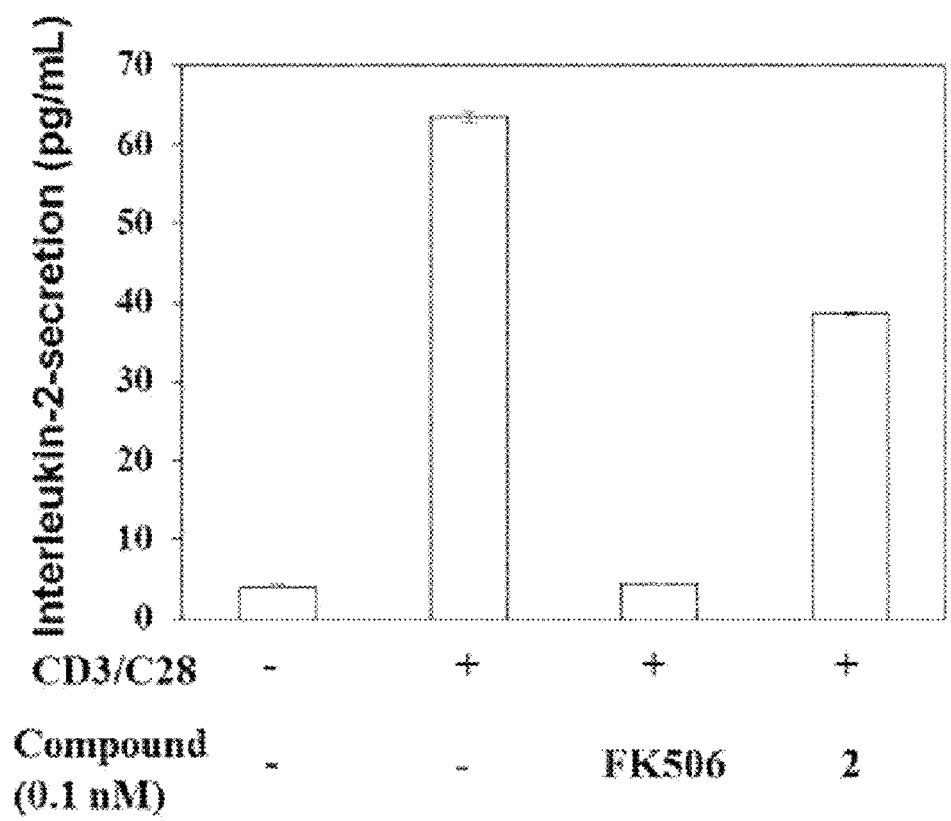
FIG. 8 shows an immunosuppressive activity of 31-O-demethyl-FK506 in comparison with FK506.

As a result, as shown in FIG. 8, when CD3/CD28-activated human T-cells were treated with FK506, the interleukin-2 secretion decreased as much as the number of CD3/CD28-inactivated human T-cells, thereby increasing the immunosuppressive activity. In contrast, when the CD3/CD28-activated human T-cells were treated with 31-O-demethyl-FK506 (marked as 2) according to the present invention, the level of interleukin-2 secretion significantly increased to reach that of the normal group, indicating a result opposite to the immunosuppressive activity of the parent molecule, FK506, and derivatives thereof.

(2) Analysis of Neuroregenerative Activity

A relative neuroregenerative property of 31-O-demethyl-FK506 compared to authentic FK506 was determined using the same method as Example 3. (2).

Figure 9A:
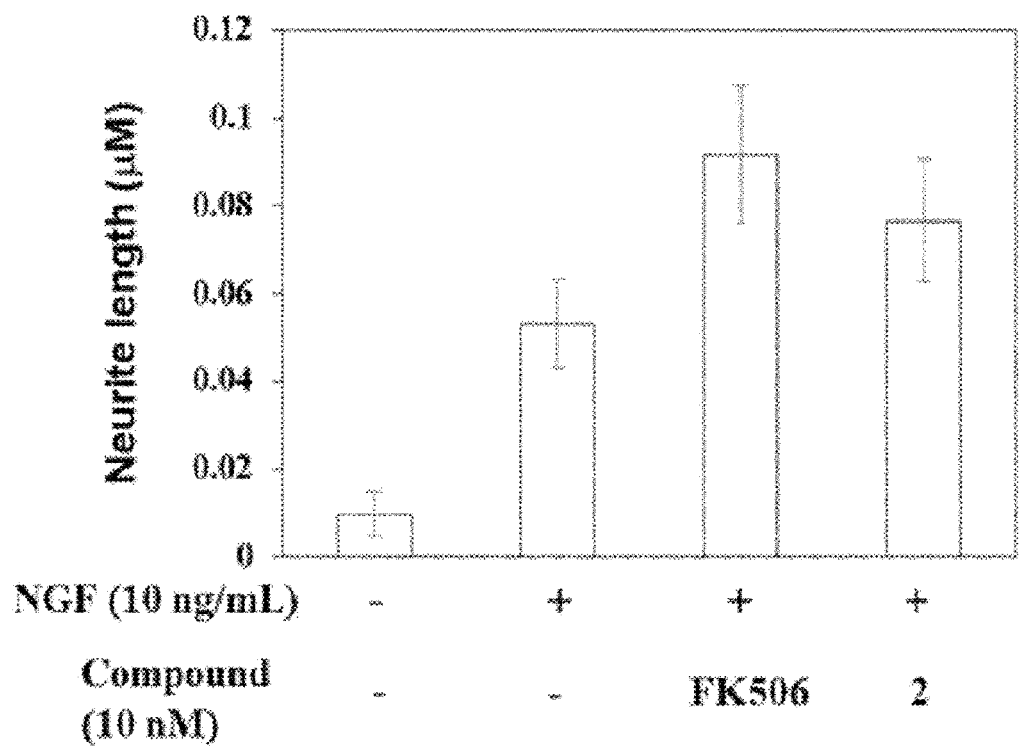
FIG. 9A shows neuroregenerative activity of 31-O-demethyl-FK506 in comparison with FK506.
Figure 9B:
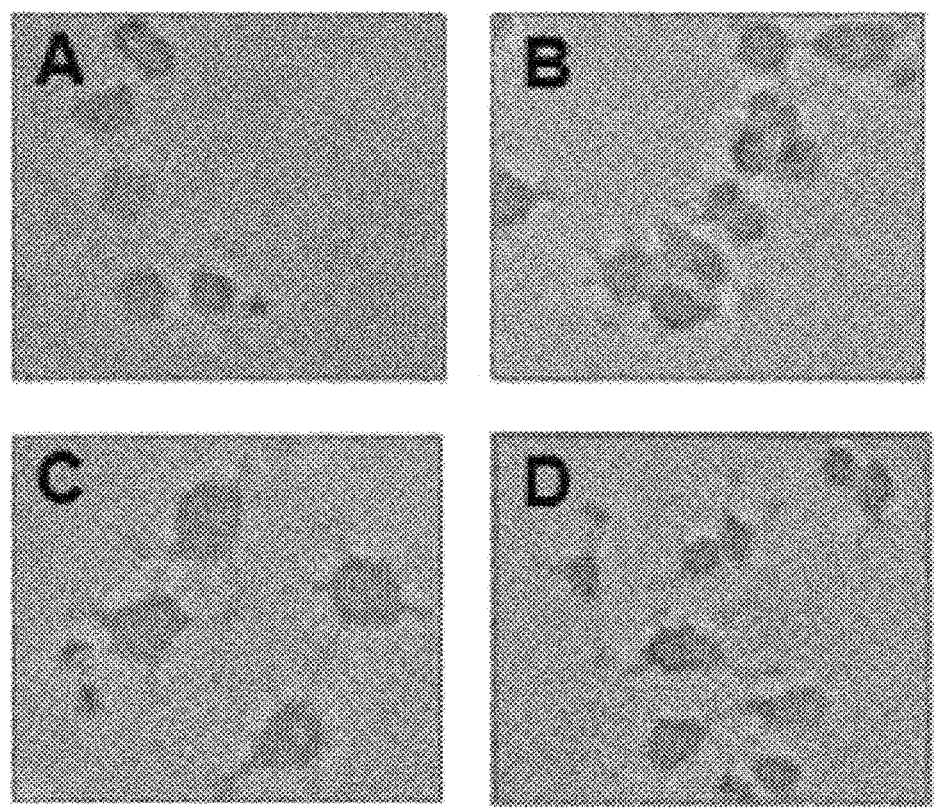
FIG. 9B shows neurites grown on PC 12 cells treated with 31-O-demethyl-FK506.

As a result, as shown in FIGS. 9a and 9b, 31-O-demethyl-FK506 (marked as 2) according to the present invention showed an excellent effect on neurite outgrowth promotion. In FIG. 9b, A refers to untreated cells, B refers to cells only treated with nerve growth factor, C refers to cells treated with nerve growth factor in the presence of FK506, and D refers to cells treated with nerve growth factor in the presence of 31-O-demethyl-FK506.

Example 5. Analysis of 9-Deoxo-31-O-Demethyl-FK506 Activity (1) Analysis of In Vitro Activity of T-Cells A relative immunosuppressive property of 31-O-demethyl-FK506 compared to authentic FK506 was determined using the same method as Example 3. (1).

Figure 10:
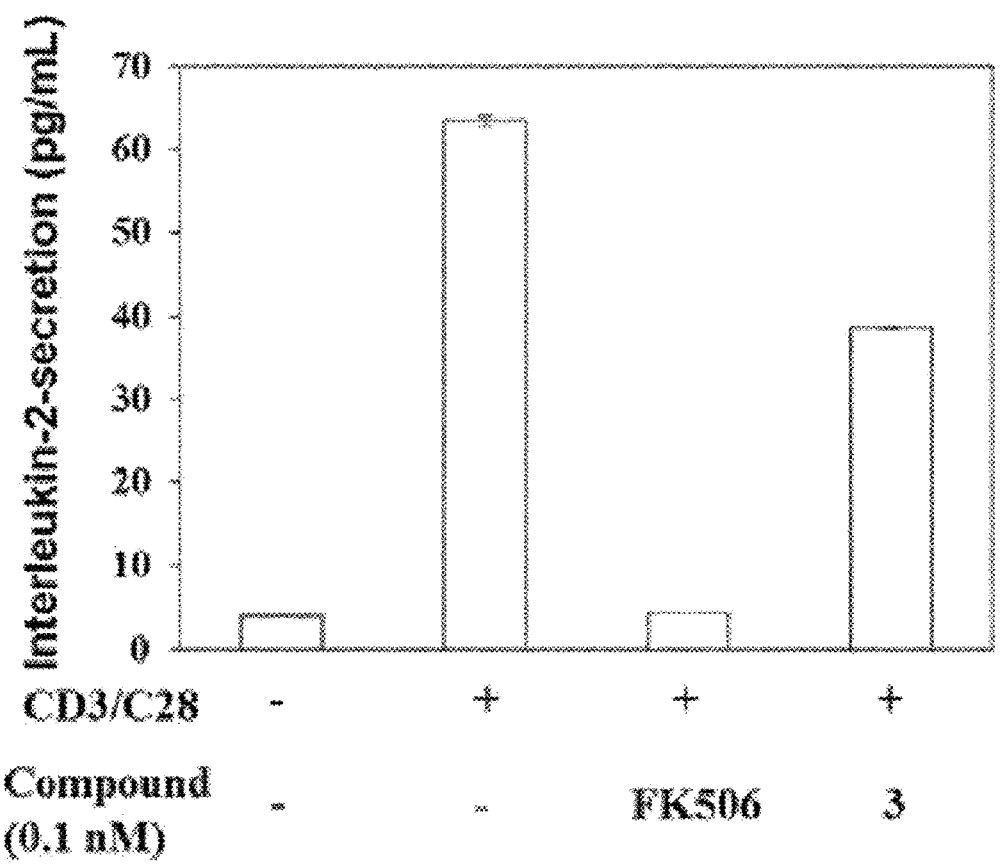
FIG. 10 shows an immunosuppressive activity of 9-deoxo-31-O-demethyl-FK506 in comparison with FK506.

As a result, as shown in FIG. 10, when CD3/CD28-activated human T-cells were treated with FK506, the interleukin-2 secretion decreased as much as the number of CD3/CD28-inactivated human T-cells, thereby increasing the immunosuppressive activity. In contrast, when the CD3/CD28-activated human T-cells were treated with 9-deoxo-31-O-demethyl-FK506 (marked as 3) according to the present invention, the level of interleukin-2 secretion significantly increased to reach that of the normal group, indicating a result opposite to the immunosuppressive activity of the parent molecule, FK506, and derivatives thereof.

(2) Analysis of Nerve Regeneration Activity

A relative nerve regeneration property of 9-deoxo-31-O-demethyl-FK506 compared to authentic FK506 was determined using the same method as Example 3. (2).

Figure 11A:
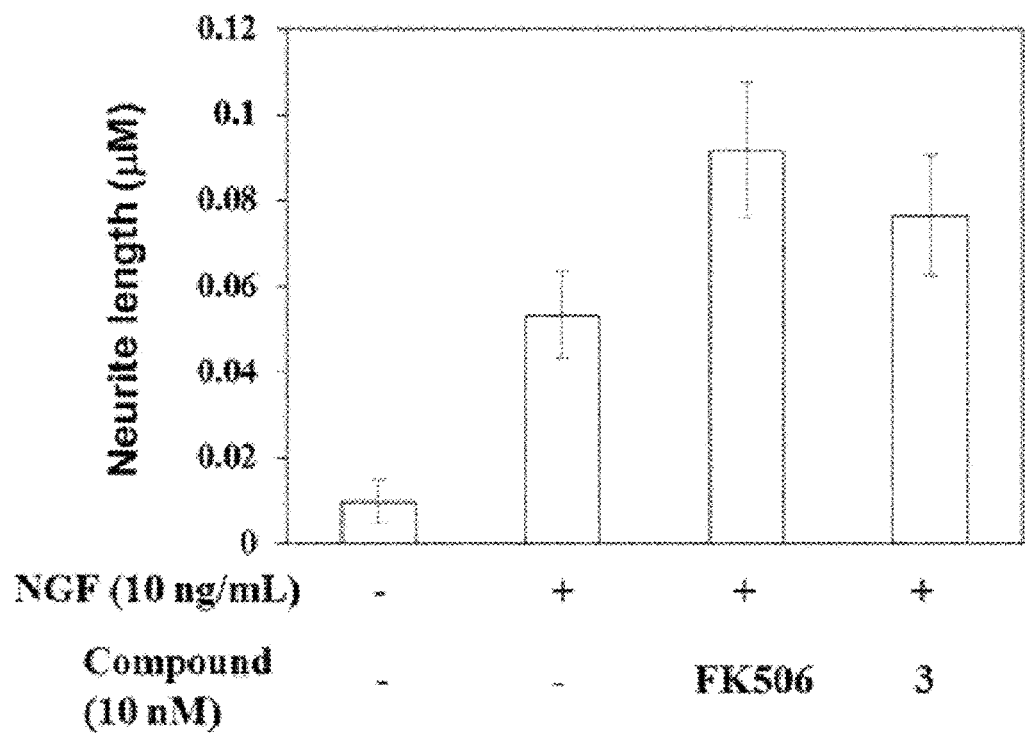
FIG. 11A shows neuroregenerative activity of 9-deoxo-31-O-demethyl-FK506 in comparison with FK506.
Figure 11B:
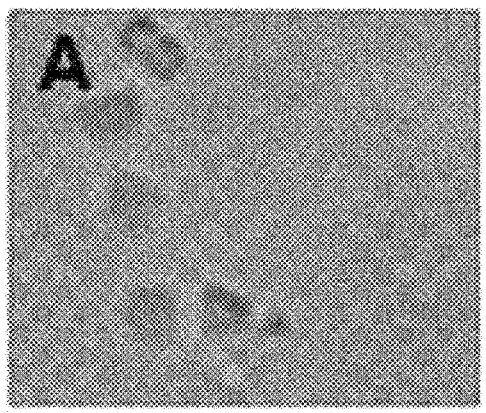
FIG. 11b shows neurites grown on PC12 cells treated with 9-deoxo-31-O-demethyl-FK506.
Figure 11B:
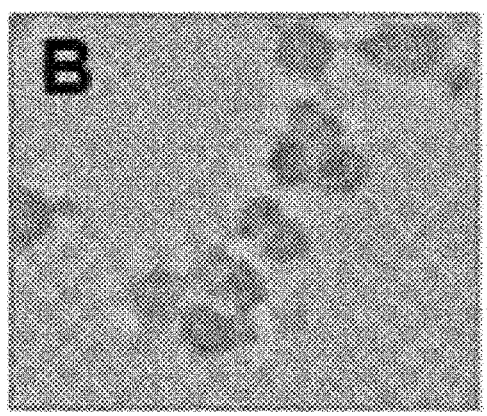
Figure 11B:
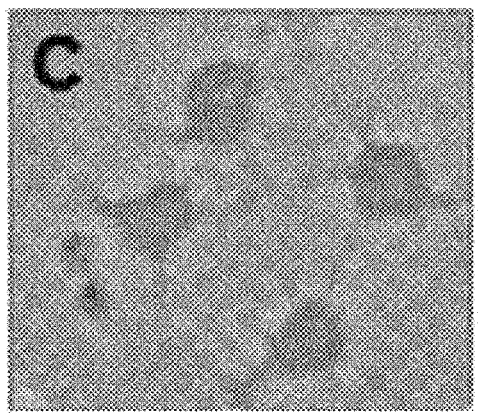
Figure 11B:
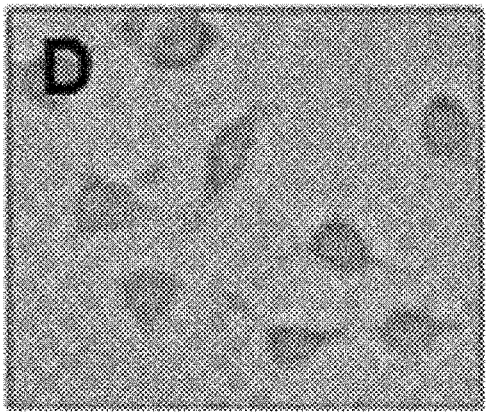

As a result, as shown in FIGS. 11a and 11b, 9-deoxo-31-O-demethyl-FK506 according to the present invention showed an excellent effect on neurite outgrowth promotion.

In FIG. 11, A refers to untreated cells, B refers to cells only treated with nerve growth factor, C refers to cells treated with nerve growth factor in the presence of FK506, and D refers to cells treated with nerve growth factor in the presence of 9-deoxo-31-O-demethyl-FK506.

Therefore, the composition according to the present invention, comprising 9-deoxo-prolyl-FK506, 31-O-demethyl-FK506, or 9-deoxo-31-O-demethyl-FK506, can promote nerve regeneration and reduce side effects in the treatment of nervous system diseases with reduced immunosuppressive activity.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

INDUSTRIAL APPLICABILITY

The composition according to the present invention can promote nerve regeneration and can be used for treating nervous system diseases with reduced immunosuppressive activity.

The invention claimed is:

1. A method for treating a nervous system disease caused by neuronal damage, comprising administering a pharmaceutical composition with reduced immunosuppressive activity to a subject having the nervous system disease, comprising one or more FK506 derivatives selected from the group consisting of 31-O-demethyl-FK506, represented by Formula 3, and 9-deoxo-31-O-demethyl-FK506, represented by Formula 4

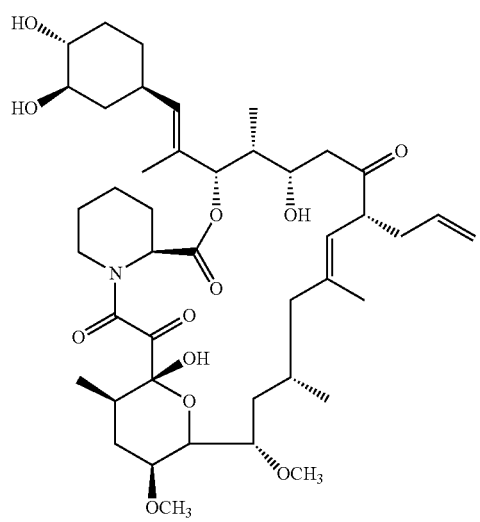

Formula 3

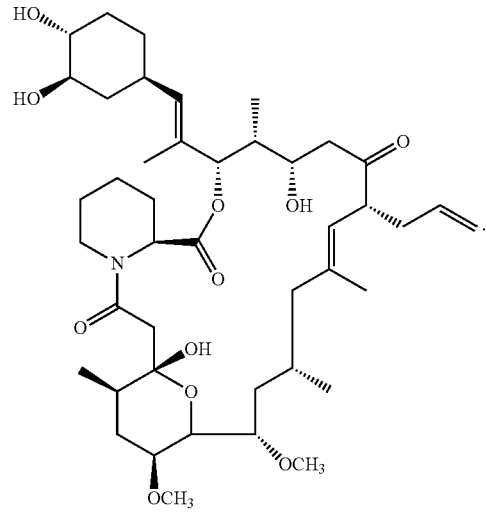

Formula 4

2. The method of claim 1, wherein the composition promotes neuroregeneration.

3. The method of claim 1, wherein the nervous system disease is a neurodegenerative disease.

4. The method of claim 1, wherein the composition increases the secretion of interleukin-2 compared to FK506.

5. A method for promoting nerve regeneration, comprising administering a pharmaceutical composition with reduced immunosuppressive activity to a subject in need, comprising one or more FK506 derivatives selected from the group consisting of 31-O-demethyl-FK506, represented by Formula 3, and 9-deoxo-31-O-demethyl-FK506, represented by Formula 4

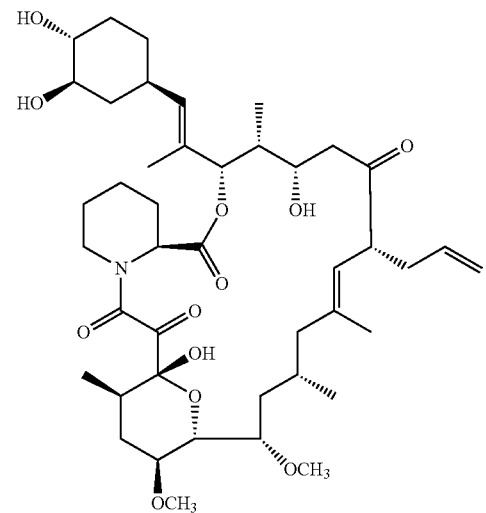

Formula 3

-continued
Formula 4
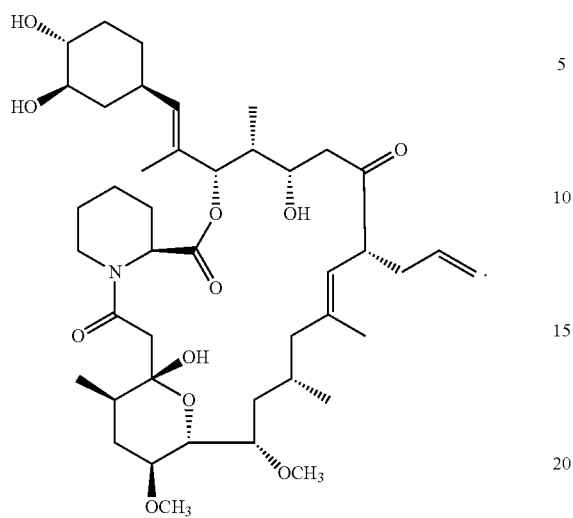
* * * * *